United States Patent [19]

Henderson, Jr.

[11] 4,216,331

[45] Aug. 5, 1980

[54] USE OF CHIRAL RHODIUM-DIPHOSPHINE CATALYST CAPABLE OF CATALYTIC REDUCTION OF A TETRAMISOLE PRECURSOR TO GIVE A SIGNIFICANT EXCESS OF THE DESIRED S-(−) ISOMER LEVAMISOLE

[75] Inventor: William A. Henderson, Jr., Stamford, Conn.

[73] Assignee: American Cyanamid Company, Stamford, Conn.

[21] Appl. No.: 9,884

[22] Filed: Feb. 6, 1979

Related U.S. Application Data

[60] Division of Ser. No. 896,254, Apr. 14, 1978, Pat. No. 4,166,824, which is a continuation-in-part of Ser. No. 806,423, Jun. 14, 1977, abandoned.

[51] Int. Cl.$^2$ ............................................. C07D 233/38
[52] U.S. Cl. .................................................... 548/320
[58] Field of Search ......................................... 548/320

[56] References Cited

U.S. PATENT DOCUMENTS

| | | | |
|---|---|---|---|
| 4,087,611 | 5/1978 | Raghu et al. | 548/320 |
| 4,090,025 | 5/1978 | Raghu et al. | 548/320 |
| 4,139,707 | 2/1979 | Raghu et al. | 548/320 |
| 4,166,824 | 9/1979 | Henderson, Jr. | 260/429 R |

*Primary Examiner*—Natalie Trousof
*Attorney, Agent, or Firm*—H. G. Jackson

[57] ABSTRACT

A soluble, chiral, rhodium-containing catalyst which permits the catalytic reduction of prochiral 3-acyl-1-2-alkoxyethyl)-4-phenyl-2-imidazolinones to chiral 3-acylimidazolidinones with a substantial excess of the desired S optical isomer. The 3-acylimidazolidinones may in turn be substantially converted to levamisole, the S isomer of tetramisole. The resolution of tetramisole to remove the R isomer is thus avoided.

1 Claim, No Drawings

USE OF CHIRAL RHODIUM-DIPHOSPHINE CATALYST CAPABLE OF CATALYTIC REDUCTION OF A TETRAMISOLE PRECURSOR TO GIVE A SIGNIFICANT EXCESS OF THE DESIRED S-(−) ISOMER LEVAMISOLE

CROSS REFERENCE TO RELATED APPLICATIONS

This is a division of application Ser. No. 896,254 filed Apr. 14, 1978, now U.S. Pat. No. 4,166,824—which is a continuation-in-part of Ser. No. 806,423, filed June 14, 1977, now abandoned.

BACKGROUND OF THE INVENTION

This invention relates to a chiral bisphosphine-rhodium complex. More specifically, this invention relates to a chiral bisphosphine-rhodium complex as a catalyst for the asymmetric reduction of a tetramisole precursor which allows the synthesis of levamisole in high optical yield.

The use of bisphosphine-rhodium complexes as a catalyst is disclosed as follows:

U.S. Pat. No. 3,949,000 discloses asymmetric diphosphines which, when reacted with a rhodium-halogen salt, produce rhodium complexes. The rhodium complexes are then used as catalysts for the hydrogenation of precursors of amino acids.

Canadian Pat. No. 977,373 discloses rhodium coordination complexes, containing a phosphine and at least one halogen ion, wherein the optical activity of the complex resides in the phosphine ligand. These complexes are useful as catalysts in the asymmetric hydrogenation of precursors of α-amino acids.

Asymmetric Catalysis by Chiral Rhodium Complexes in Hydrogenation and Hydrosilylation Reactions, H. B. Kagan, "Pure and Applied Chemistry," 43, p. 402 (1976) discloses asymmetric catalytic reduction of optically active enamides and precursors of α-amino acids using a chiral diphosphine rhodium complex as a homogeneous catalyst.

All of the above references are incorporated herein by reference.

Also, U.S. Patent Application Ser. No. 739,923 filed Nov. 8, 1976, now U.S. Pat. No. 4,087,611 which is a CIP of U.S. Patent Application Ser. No. 680,302, filed Apr. 26, 1976 now abandoned, discloses a process of using a chiral rhodium-diphosphine catalyst to directly manufacture an optically active levamisole. See, e.g. U.S. Patent Application Ser. No. 739,923, page 9.

The utility of the compound of this invention: chiral-2,3-Bis(diphenylphosphinomethyl)bicyclo[2.2.1]heptane is as an intermediate in the manufacture of a chiral rhodium-diphosphine catalyst which is useful in the reduction of a tetramisole precursor to give a significant excess of the desired S-(-) isomer, levamisole. The chiral rhodium-diphosphine catalyst and the process of using the catalyst in the reduction of the tetramisole precursor is also novel.

SUMMARY AND DESCRIPTION OF THE INVENTION

The compound trans-2,3-Bis(diphenylphosphinomethyl)bicyclo[2.2.1]heptane and its chiral enantiomers has been discovered.

A chiral catalyst prepared by reacting a chiral enantiomer of the compound described in the paragraph above with [Rh(COD)X]$_2$, wherein X is Cl, Br or I is also within the scope of this invention. In a preferred embodiment, the chiral catalyst is prepared by reacting a chiral enantiomer of the compound described in the paragraph above with about ½ mole of [Rh(COD)I]$_2$.

A method for the preparation of optically active 3-acyl derivatives of 1-(2-alkoxyethyl-4-phenyl-2-imidazolidones from 3-acyl derivatives of 1-(2-alkoxyethyl)-4-phenylimidazolin-2-one by hydrogenating at a suitable temperature and pressure in the presence of a solvent, the improvement comprising: hydrogenating in the presence of the chiral catalyst prepared by reacting the compound trans-2,3-Bis(diphenylphosphinomethyl)bicyclo[2.2.1]heptane and its chiral enantiomers with [Rh(COD)X]$_2$, wherein X is Cl, Br or I has also been discovered.

The invention is summarized in Sequence 1 and Sequence 2 of the flowsheet. 2R,3R-2,3-Bis(diphenylphosphinomethyl)bicyclo[2.2.1]heptane, Formula (1) was synthesized by the Sequence 1. When added in ethyl acetate solution to chloro (1,5-cyclooctadiene)rhodium (I) dimer in the ratio two phosphorus atoms to one rhodium atom, a complex was formed which acted as a catalyst for the asymmetric reduction of 1-(2-methoxyethyl)-3-acetyl-4-phenyl-4-imidazolin-2-one (2) to the imidazolidinone (3) with a 41% ee of the R-(+) isomer. By % ee is meant the percent, in absolute values, of the enantiomeric excess of the isomer. In a mathematical formula, this is defined as:

$$\% \, ee = \left| \frac{R-S}{R+S} \right| \times 100$$

where R and S are the optical isomers. When iodo(1,5-cyclooctadiene)rhodium (I) dimer is used, the R-(+) isomer is formed in 57% ee. The halogen used in the rhodium salt can also be bromo(1,5-cyclooctadiene)rhodium (I). In the preferred embodiment, iodo(1,5-cyclooctadiene)rhodium(I) is used.

The complex is prepared in situ. Solvents which can be used to prepared the complex include, but are not limited to, acetone, benzene, isopropanol, ethanol, and tert-butanol. As a general rule, it can be stated that any solvent can be used which will prepare the complex and which will not inhibit the asymmetric reduction of Formula (2) to Formula (3).

The method for the preparation of optically active 3-acyl derivatives of 1-(2-alkoxyethyl-4-phenyl-2-imidazolidones from 3-acyl derivatives of 1-(2-alkoxyethyl)-4-phenylimidazolin-2-one is by hydrogenating at a suitable temperature and pressure in the presence of a solvent as more fully described in the Examples. The improvement of this invention comprises hydrogenating in the presence of a Rh(I) complex prepared by reacting about 2 moles of an optically active 2S,3S isomer of Formula (I) with about 1 mole of (RhCODX)$_2$; wherein X is Cl, Br or I.

Use of the 2S,3S isomer of Formula (1) gives the desired S-(−) isomer, levamisole.

The effect of solvent, the halogen used in the rhodium salt, temperature, hydrogen pressure and time can all affect the % ee obtained in the product. Therefore these parameters should be considered in using Sequence 2.

Sequence 1

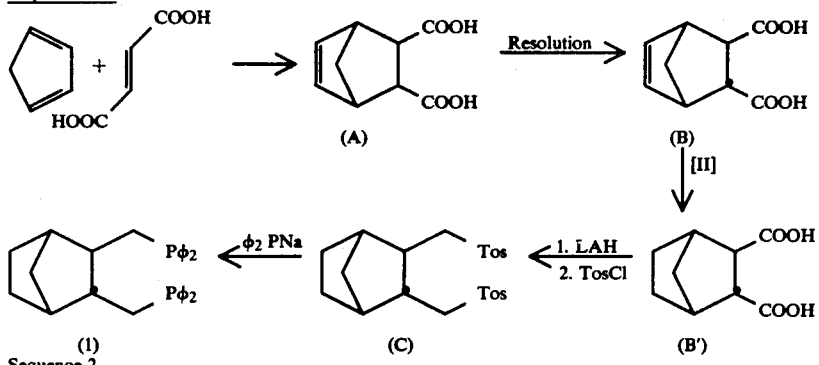

Sequence 2

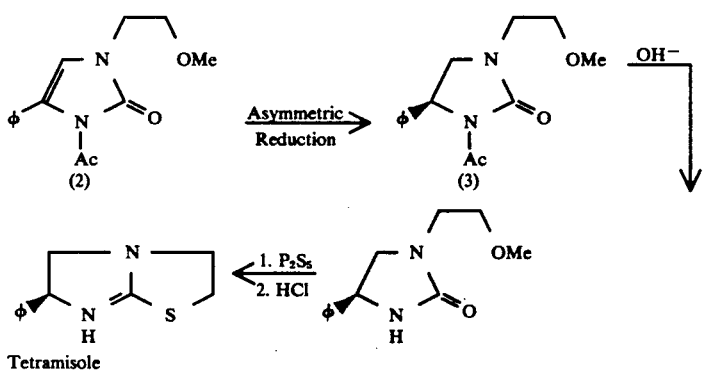

DETAILED DESCRIPTION OF THE INVENTION

EXAMPLE 1

Synthesis and Resolution of trans-Bicyclohept-5-ene-2,3-dicarboxylic acid

Trans-Bicyclo[2.2.1]hept-5-ene-2,3-dicarboxylic acid, Formula (A) in Sequence 1, was prepared by the method of H. Koch, J. Kotalan and H. Markut, Monatshefte, 96, 1646 (1865). Resolution was accomplished by adding a solution of 34.3 g (0.188 moles) of the diacid in 150 ml of ethanol to a solution of 30.8 g (0.086 moles) of quinine dihydrate in 75 ml of ethanol. The mixture was allowed to stand overnight and the precipitate then filtered. The precipitated salt was triturated with 100 ml of boiling ethanol and filtered again. The remaining salt was decomposed with 10% aqueous sodium hydroxide solution, the quinine extracted with methylene chloride, and the free acid precipitated from the aqueous solution by addition of hydrochloric acid. After washing the product with water and drying under vacuum over phosphorus pentoxide, 11.3 g of 2R,3R[2.2.1]bicyclohept-5-ene-2,3-dicarboxylic acid, Formula (B) in Sequence 1, is obtained $(\alpha)_D^{27°} = -122°$ (c=2, acetone). Pincock et al (R. E. Pincock, M-M Tong and K. R. Wilson, J. Am. Chem. Soc., 93, 1669 (1971) report the rotation of the resolved diacid to be 137° and 147° (two preparations) in acetone; hence, the present diacid appears to be approximately 86% pure.

EXAMPLE 2

2R,3R[2.2.1]Bicycloheptane-2,3-dicarboxylic acid

The diacid of Example 1, 10.0 g (0.055 moles), was dissolved in a solution of 12.6 g of sodium bicarbonate in 200 ml of water, After addition of 400 mg of 10% palladium on carbon, the mixture was hydrogenated in a Parr apparatus. Hydrogen uptake was complete at 5 hours. The product was filtered and then acidified with hydrochloric acid. The water was evaporated and the residue extracted with acetone. Evaporation of the acetone gave 9.32 g of the desired title diacid.

EXAMPLE 3

2R,3R-2,3-bis(Hydroxymethyl)bicyclo[2.2.1]heptane.

A solution of 9.0 g (0.049 moles) of the diacid product of Example 2 in 80 ml of dry tetrahydrofuran was added at room temperature under nitrogen to a stirred suspension of 5.0 g of lithium aluminum hydride in 10 ml of tetrahydrofuran. The mixture was stirred for one hour and then heated to 55°-60° for two hours. Excess hydride was decomposed with saturated ammonium chloride solution. Sodium sulfate was added, and the solids thus obtained extracted with ether in a Soxhlet extractor for 24 hours. Evaporation of the ether gave 7.3 g of 2R,3R-2,3-bis(hydroxymethyl)bicyclo[2.2.1]heptane, Formula (B') in Sequence 1, a thick oil.

EXAMPLE 4

2R,3R-2,3-bis(Hydroxymethyl)bicyclo[2.2.1]heptane ditosylate.

To a solution of 6.25 g (0.040 moles) of the diol of Example 3 in 45 ml of dry pyridine was added at 0° 16.0 g (0.084 moles) of tosyl chloride. The mixture was stirred at 0° for 24 hours, and water then added to dissolve the pyridine hydrochloride formed and to precipitate the product. Filtration, washing with water and drying over phosphorus pentoxide afforded 17.1 g of the product, Formula (C) in Sequence 1, as white powder, m.p. 93°-95°.

EXAMPLE 5

2R,3R-2,3-Bis(diphenylphosphinomethyl)bicyclo[2.2.1-]heptane

All subsequent operations were carried out under nitrogen. A mixture of 10.0 g (0.045 moles) of diphenyl chlorophosphine, 4.15 g of sodium and 115 ml of dry dioxane was refluxed with vigorous stirring with a wire stirrer for eight hours. The product mixture, containing sodium diphenylphosphide and unreacted sodium, was cooled to 0° and a solution of 6.96 g (0.015 moles) of the ditosylate product of Example 4 in 40 ml of dry tetrahydrofuran was slowly added. The mixture was stirred at room temperature for two hours, filtered, and the solvent removed under vacuum. The resultant oil was taken up in water and hexane, and the organic portion chromatographed on basic alumina using hexane. The product, Formula (1) in Sequence 1, 3.0 g, was obtained as a viscous oil which would not crystallize.

EXAMPLE 6

The following illustrates the preparation of the chiral rhodium diphosphine catalyst.

In a 100 ml flask is placed under nitrogen 146 mg (0.30 mole) of the diphosphine of Formula (1) as prepared in Example 5, 65 mg (0.25 moles) of [Rh(COD)Cl]$_2$ and 20 ml of oxygen free ethyl acetate at ambient temperature and pressure. A deep orange solution is obtained.

EXAMPLE 7

1-(2-Methoxyethyl)-4-phenyl-4-imidazolin-2-one

Phenacyl bromide (60 g.), in 200 ml. of methylene chloride, is added over one hour to 2-methoxyethylamine (52 g.) in 100 ml. of methylene chloride, and cooled with an ice bath. The mixture is stirred for two hours at 0° C. Water (400 ml.) is added and the organic layer is separated, dried over anhydrous sodium sulfate and concentrated under aspirator vacuum (at room temperature). The viscous oil (260 g.) is dissolved in methanol (200 ml.), cooled to 0° C. and acetic acid (80 ml.) and potassium cyanate (30 g.) is added. The mixture is refluxed for 90 minutes, the solvent removed under reduced pressure and the residue is taken up in 600 ml. of chloroform and washed with saturated sodium bicarbonate solution. The chloroform layer is washed, dried over sodium sulfate and concentrated to give a semisolid. Trituration with ether and filtration yield the title product as a yellow crystal; m.p. 152°-153° C.

EXAMPLE 8

1-(2-methoxyethyl)-4-phenyl-4-imidazolin-2-one

Phenacyl bromide (199 g.), in 400 ml. of chloroform is added over one half hour to a mixture of 2-methoxyethylamine (82 g) and triethylamine (152 g.) in 200 ml. of chloroform at 0° C. The mixture is stirred for two hours at 0°-10° C. Water (400 ml.) is added and the organic layer is separated and washed with another 400 ml. of water. The chloroform layer is cooled to 0° C. with an ice bath and glacial acetic acid (72 g.) potassium cyanate (89 g.) and methanol (100 ml.) are added. The mixture is refluxed for ninety minutes, cooled and washed with saturated sodium bicarbonate solution, and the organic layer is dried over anhydrous sodium sulfate and then concentrated to give a semisolid. Trituration with 300 ml. of ether and filtration gives the title product as a yellow crystal; m.p. 152°-154° C.

EXAMPLE 9

1-(2-methoxyethyl)-3-acetyl-4-phenyl-4-imidazolin-2-one

Approximately 21.8 g of 1-(2-methoxyethyl)-4-phenyl-4-imidazolin-2-one and 120 ml. of acetic anhydride is refluxed together for four hours. The acetic anhydride is distilled out at reduced pressure. The residual semisolid is recrystallized from ethyl acetate to yield the title compound Formula (2) in Sequence 2 as a white solid; m.p. 81°-82° C.

EXAMPLE 10

A mixture of 1.30 g (5.9 millimoles) of the product of Example 9, 146 mg. (0.297 millimoles) of the R,R diphosphine product of Example 5 and 65 mg. (0.25 millimoles) of rhodium cyclooctadiene chloride [Rh(COD)Cl]$_2$, calculated as monomer, in 20 ml. of oxygen free ethyl acetate was placed under nitrogen in a glass lined autoclave. Hydrogen was admitted to a pressure of 1000 psi, and the mixture heated to 60° for 8 hours. Analysis of the hydrolysis product of the reaction showed an enantiomeric excess (ee) of the R isomer of 36%. Corrected for the optical purity (86%) of the resolved diacid from which the chiral diphosphine was prepared, the ee is 41%.

EXAMPLE 11

Using the same ratios of reactants and the same conditions as in Example 10 except that [Rh(COD)Br]$_2$ was used in place of [Rh(COD)Cl]$_2$, the ee was 40% (56% corrected).

EXAMPLE 12

Using the same ratios of reactants and the same conditions as in Example 10 except that [Rh(COD)I]$_2$ was used in place of [Rh(COD)Cl]$_2$, the ee was 50% (57%, corrected).

EXAMPLE 13

Using the same ratios and the same conditions as in Example 12 except that the reaction was run at 500 psi hydrogen and 27° for 24 hours, the ee was 53% (61%, corrected).

EXAMPLE 14

Using the same ratios of reactants and the same conditions as in Example 12 except that the reaction was run at 200 psi hydrogen and 27° for 24 hours, reaction was 70% complete, and the ee was 54% (62%, corrected).

EXAMPLE 15

Using the same ratios of reactants and the same conditions as in Example 12 except that a 3:1 ratio of benzene and i-propanol was used as solvent, the ee was 53% (61%, corrected).

EXAMPLE 16

Cinchonine Salt of (2S,3S)[2.2.1]Bicyclohept-5-ene-2,3-dicarboxylic acid

In a 1-liter flask was placed 81.8 g (0.278 moles) of cinchonine (Tridom Chem.) and 300 ml of methanol. The milky suspension was heated to boiling and 50.65 g (0.278 moles) of bicyclo[2.2.1]heptane-2,3-dicarboxylic acid was added. All of the solid dissolved with swirling to give a clear amber solution. Acetone (250 ml) was added and the volume was reduced to 600 ml by boiling on a steam bath. The solution was then allowed to stand overnight (18 hours) at room temperature. The mother liquor was decanted from the mass of crystals that had formed and the crystals were washed with a small amount of acetone. Reduction of the mother liquor volume to 350 ml and room temperature storage overnight gave a third crop. These crops were combined and recrystallized from 3/2 V/V methanol/acetone to give a total of 59 g (88%) of the desired enantiomeric salt. Treatment of the combined mother liquors with aqueous ammonium hdroxide produced a precipitate containing 90% of the cinchonine present.

EXAMPLE 17

(2S,3S)[2.2.1]Bicyclohept-5-ene-trans-2,3-dicarboxylic acid

To a suspension of 33.9 g (0.0730 moles) of a finely ground 1:1 salt of cinchonine and (2S,3S)[2.2.1]bicyclohept-5-ene-trans-2,3-dicarboxylic acid in 400 ml of hot (80° C.) water was added 50 ml of conc. $NH_4OH$ with stirring. The addition caused a voluminous precipitation of cinchonine to occur. The mixture was heated for 2 hours further to ensure complete decomposition of the salt and was then filtered, washed with water, and air-dried. The filter cake weighed 20.2 g (96% cinchonine recovery) and was suitable for reuse (m.p. 265°, as reported). The aqueous filtrate was acidified with conc. HCl, saturated with NaCl and cooled in ice. The crystallized product obtained, 12.0 g (93%), has an $\alpha_D = +150°$ (C=1, acetone).

EXAMPLE 18

(2S,3S)[2.2.1]Bicycloheptane-trans-2,3-dicarboxylic acid

To 150 ml of ethanol in a 500 ml Parr hydrogenation bottle was added 10.0 g (0.0549 moles) of (2S,3S)[2.2.1]bicyclohept-5-ene-trans-2,3-dicarboxylic acid (which completely dissolved) and 500 mg of 10% Pd/charcoal (Engelhard). The mixture was placed in a Parr shaker under 40 psig of $H_2$. The solution absorbed hydrogen very rapidly and the uptake was largely completed after 20 minutes. The mixture was filtered to remove the catalyst and the ethanol was evaporated to give 9.9 g (98%) of white crystalline product, m.p. 161°-163° C., $\alpha_D = +26.6°$ in acetone.

EXAMPLE 19

(2S,3S)-2,3-bis(Hydroxymethyl)bicyclo[2.2.1]heptane

In a 500 ml 3-neck flask at −5° C. under $N_2$ was placed 100 ml of THF (freshly opened bottle) and 5.0 g (0.1315 moles) of LAH (Ventron, fresh package). A solution of 9.0 g (0.05 moles) of (2S,3S)[2.2.1]bicycloheptane-trans-2,3-dicarboxylic acid in 30 ml of THF was added dropwise over 30 minutes under $N_2$ maintaining the temperature at or below 0° C. The stirred solution was allowed to warm to room temperature and held at room temperature for 1 hour, then cautiously warmed to reflux and refluxed for 2 hours. Note: Heating to reflux must be done cautiously because a strong exotherm occurred just prior to the onset of refluxing. After cooling to room temperature, the reaction mixture was cautiously poured into 250 ml of cold 10% HCl and saturated with NaCl and extracted with 3×200 ml of diethyl ether (methylene chloride may be substituted for diethyl ethyl). The extracts were combined, dried over $MgSO_4$, and the solvent evaporated to give 7.5 g (>96%) of a viscous oil which solidified on standing (m.p. 58° C.) The infrared spectrum showed no detectable carbonyl.

EXAMPLE 20

(2S,3S)-2,3-bis(Hydroxymethyl)bicyclo[2.2.1]heptane ditosylate

In a 200 ml round bottom flask capped with a $CaCl_2$ drying tube was placed 7.2 g (0.0461 moles) of (2S,3S)-2,3-bis(hydroxymethyl)bicyclo[2.2.1]heptane (m.p. 58° C.) together with 45 ml of pyridine and 18.4 g (0.096 moles) of p-toluenesulfonyl chloride. The mixture was cooled in an ice bath and stirred for 3 hours and then diluted with 10 ml of $H_2O$. The precipitate which formed was filtered and washed to remove pyridine. The solid was recrystallized from ethanol to give 17.2 g (92%) of fine white needles, m.p. 100°-101° C., $\alpha_D = +32.2°$ C.

EXAMPLE 21

(2S,3S)-2,3bis(Diphenylphosphinomethyl)bicyclo[2.2.1]heptane

A flame-dried 50 ml flask was purged with argon (Ar) and 140 mg of lithium ribbon cut into thin slivers (12 pieces) was added (transferred in a glove bag). To the lithium was added 7 ml of THF (freshly distilled from LAH under Ar and stored under Ar) via syringe. To this mixture was added 2.358 g (0.009 moles) of triphenylphosphine (under Ar) and rapid stirring was initiated. A red coloration, indicating the formation of lithium diphenylphosphide, was observed. After 5 hours of stirring at room temperature, no lithium metal could be detected. The reaction product was treated with 750 mg (0.009 moles) of tertiary butyl chloride (dried over $MgSO_4$, distilled and stored under nitrogen before use) then briefly warmed to reflux. After 45 minutes of stirring at room temperature the mixture was re-cooled in an ice-salt bath (−4° C.) and 1.859 mg (0.004 moles) of (2S,3S)2,3-bis(hydroxymethyl)bicyclo[2.2.1]heptane ditosylate in 6 ml of THF was added over 30 minutes. The mixture was warmed to room temperature and stirred for 18 hours. Addition of 3 ml of $H_2O$ changed the color of the solution from dark red to pale yellow. The reaction mixture was partitioned between 50 ml of $H_2O$ and 50 ml of methylene chloride. The aqueous layer was separated and washed with 25 ml of methylene chloride. The methylene chloride fractions were combined, dried over $MgSO_4$ and chromatographed on 25 g of neutral alumina, eluting with 100 ml of additional methylene chloride. The entire eluent was concentrated and vacuum pumped (100° C., 0.1 mm, 6 hours) to yield 1.82 g (92%) of a viscous oil, $\alpha_D = -12°$. The infrared spectrum of this oil showed no detectable P-H (~2100 $cm^{-1}$), P-O (~1185 $cm^{-1}$) or unreacted tosylate (~1380 $cm^{-1}$) but did show traces of OH or NH (3450 $cm^{-1}$).

EXAMPLE 22

A mixture of 1.10 g (0.005 moles) of the product of Example 9, 46.0 mg (0.093 millimoles) of the S,S diphosphine product of Example 21 and 28.9 mg. (0.086 millimoles) of rhodium cyclooctadiene iodide [Rh(COD)I]$_2$, calculated as monomer, in 20 ml of oxygen free ethyl acetate was placed under nitrogen in a glass lined autoclave. Hydrogen was admitted to a pressure of 1000 psi, and the mixture heated to 60° C. for 8 hours. Analysis of the hydrolysis product of the reaction showed an enantiomeric excess (ee) of the S isomer of 63%.

I claim:

1. In a method for the preparation of optically active 3-acyl derivatives of 1-(2-alkoxyethyl)-4-phenyl-2-imidazolidones from 3-acyl derivatives of 1-(2-alkoxyethyl)-4-phenylimidazolin-2-one by hydrogenating in the presence of a solvent, the improvement comprising:

hydrogenating in the presence of a chiral catalyst prepared by reacting a chiral enantiomer of the compound trans-2,3-Bis(diphenylphosphinomethyl)bicyclo[2.2.1]heptane with [Rh(COD)X]$_2$, wherein X is Cl, Br or I.

* * * * *